United States Patent
Baker et al.

(10) Patent No.: US 10,561,525 B2
(45) Date of Patent: Feb. 18, 2020

(54) MODULAR PROSTHESIS COOLING SYSTEMS

(71) Applicant: LETO Solutions, Inc., San Antonio, TX (US)

(72) Inventors: Sean Baker, San Antonio, TX (US); Gary Walters, San Antonio, TX (US)

(73) Assignee: LETO SOLUTIONS, INC., San Antonio, TX (US)

( * ) Notice: Subject to any disclaimer, the term of this patent is extended or adjusted under 35 U.S.C. 154(b) by 0 days.

(21) Appl. No.: 15/741,495

(22) PCT Filed: Jul. 1, 2016

(86) PCT No.: PCT/US2016/040733
§ 371 (c)(1),
(2) Date: Jan. 2, 2018

(87) PCT Pub. No.: WO2017/004540
PCT Pub. Date: Jan. 5, 2017

(65) Prior Publication Data
US 2018/0214299 A1    Aug. 2, 2018

Related U.S. Application Data

(60) Provisional application No. 62/187,698, filed on Jul. 1, 2015.

(51) Int. Cl.
*A61F 2/80* (2006.01)
*A61F 7/00* (2006.01)

(52) U.S. Cl.
CPC ............... *A61F 7/007* (2013.01); *A61F 2/80* (2013.01); *A61F 2007/0051* (2013.01); *A61F 2007/0075* (2013.01)

(58) Field of Classification Search
CPC ............................. A61F 2/80; A61F 2002/805
See application file for complete search history.

(56) References Cited

U.S. PATENT DOCUMENTS

| | | | |
|---|---|---|---|
| 2,533,404 A * | 12/1950 | Sharp | A61F 2/80 220/203.04 |
| 7,670,385 B2 * | 3/2010 | Klein | A61F 2/72 623/25 |
| 2007/0112439 A1 * | 5/2007 | Panucialman | A61F 2/80 623/26 |
| 2012/0302323 A1 * | 11/2012 | Gagner | G07F 17/3202 463/25 |
| 2013/0079893 A1 * | 3/2013 | Allemand | A61F 2/7812 623/36 |
| 2016/0030207 A1 * | 2/2016 | Walters, Jr. | A61F 2/80 623/33 |

OTHER PUBLICATIONS

Oandp.com, Leto Solutions Honored as One of the Ten Best Companies, Mar. 3, 2014 (Year: 2014).*

* cited by examiner

*Primary Examiner* — Bruce E Snow
(74) *Attorney, Agent, or Firm* — Pizarro Allen PC

(57) ABSTRACT

A modular prosthesis cooling system may comprise a port disposed in the wall of a prosthesis socket, and a plug module removable disposed in the port. The plug module may comprise cooling element, such as a TEC, and a heat-dissipation element, such as a heat sink or fan. A protective heat-dissipating shroud may be disposed about plug module. The prosthesis socket wall may comprise a heat-conductive layer in a heat-exchange relationship with the cooling element.

9 Claims, 3 Drawing Sheets

MODULAR PROSTHESIS COOLING SYSTEMS

CROSS-REFERENCE TO RELATED APPLICATION

This application claims priority to U.S. Provisional Patent Application 62/187,698 entitled "Modular Prosthesis Cooling System" filed Jul. 1, 2015, which is hereby entirely incorporated herein by reference.

FIELD

The disclosed method and apparatus generally relate to prosthesis cooling.

BACKGROUND

Amputees may use a variety of prostheses designed to support their residual limb during ambulation and other activities. The residual limb may include bone, muscle, tissue, and skin. Prosthetic limbs generally include a socket and a liner designed to fit over the residual limb. The socket may be a relatively rigid shell that encases the residual limb. The liner may provide a flexible cushion between the residual limb and socket, and act as a "second skin" between the residual limb and socket. The liner may provide a more consistent connection between the residual limb and the prosthetic socket, and increase the variety of motions an amputee may perform.

Sockets may be made of a variety of materials such as resin, acrylic, carbon fiber, and other suitable materials. Sockets may comprise one or more rigid layers and in some cases a flexible inner socket may be used between the hard socket and liner to provide a better connection with more dynamic linkage between the residual limb and prosthesis. An inner socket may provide greater surface area for connection with a rigid socket, improve the vacuum for vacuum-assisted suspension sockets, and reduce friction against the residual limb.

Sockets and liners are typically constructed from materials that exhibit poor heat transfer properties and are not gas permeable, which results in the wearer's body heat being trapped inside the socket. Thus, despite advances in liners and sockets, there exists an issue of high temperature environments developing in the socket of prosthetic devices. If heat builds up to the point of sweating, the prosthetic wearer is at risk of skin degradation, discomfort, decreased mobility, and poor linkage between the prosthesis and residual limb. This situation necessitates the use of a cooling system to improve amputee comfort and usability of prosthetic devices.

Prosthetic limbs are generally custom made to fit an individual's residual limb by a prosthetist. A prosthetist may evaluate the size and condition of the residual limb, patient health and lifestyle, and other factors in designing a suitable prosthetic. Such design may include a prosthetic cooling system to resolve the temperature problem as previously described. A prosthetist may select a cooling system as described herein for the inclusion in the prosthesis during fabrication. One method of alleviating heat retention is through the application of thermoelectric elements (TEC) to cool the socket. Due to the curved nature of a prosthetic socket and the typical flat planar geometry of TECs, the method of coupling the TEC to the socket requires a specialized TEC-socket interface. Furthermore, for the TEC to be more effective in cooling the residual limb, the wall of the socket may need to be thinned in the area of the TEC. Thinning the socket wall in localized areas may weaken the structural integrity of the socket, and increase the possibility of a crack developing. Also, permanently coupling a TEC to a prosthesis socket makes removing the TEC impossible without damaging the socket. If an installed TEC fails, a new socket may have to be fabricated to replace the existing socket with nonworking TECs.

There remains a need for a modular prosthetic cooling system that may be adapted for removable mounting to a prosthetic socket substantially without compromising the structural integrity of the prosthesis socket.

SUMMARY

A modular prosthesis cooling system may comprise a port configured for mounting to a prosthesis socket, and a plug module configured for removable mounting to the port, the plug module comprising a cooling element.

DETAILED DESCRIPTION

Figure 1:
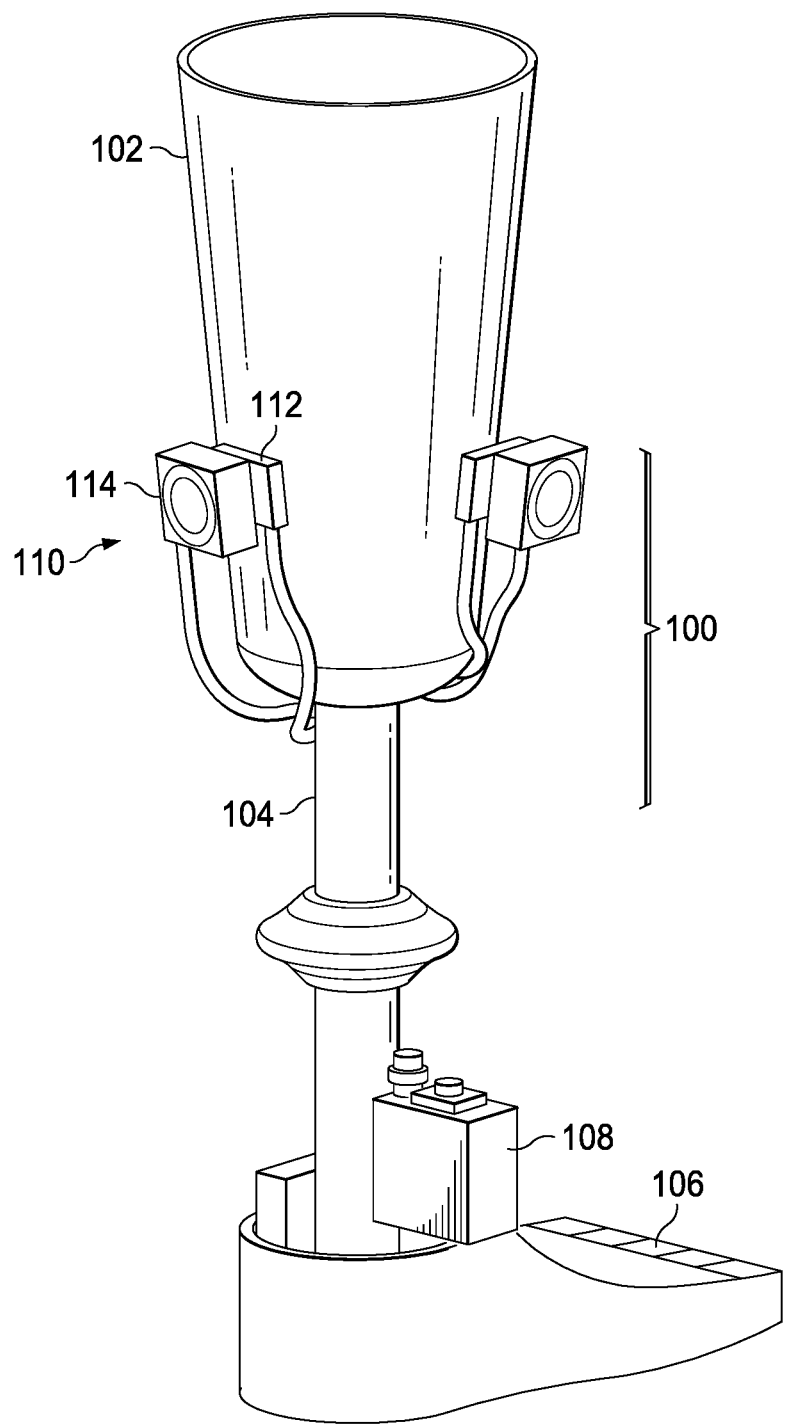
FIG. 1 illustrates an embodiment of a prosthesis with a modular cooling system mounted thereto.

The embodiment of FIG. 1 is disclosed in connection with an example prosthesis 100 for transtibial (below the knee or BK) amputated limb (not shown). It should be clear, however, that the embodiments disclosed herein may be suitably used with any other amputated limb, whether an upper limb or lower limb. As may be seen in the embodiment in FIG. 1, the prosthesis 100 may include a socket 102, a pylon 104, and a foot 106. Any suitable system may be used to assist the wearer in retaining prosthesis linkage to the residual limb. For example, a vacuum system may be used, and may be provided in line with the pylon 104, or attached externally to the pylon 104, depending on the system used (not shown).

A modular prosthesis cooling system 110 may be removably mounted to the prosthesis 100. In the embodiment in FIG. 1, the modular prosthesis cooling system 110 may include one or more thermoelectric cooling elements (TEC or Peltier device) 112. Each TEC 112 may comprise a cold side surface and a hot side surface on opposing sides of the TEC 112. Each TEC 112 may be oriented in such a way that the cold side surface may receive heat from the residual limb (not shown). The hot side surface of the TEC 112 may be oriented to directly or indirectly dissipate heat to atmosphere. In such embodiments, the cold side surface may generally face the interior of the socket where a residual limb may be exposed, and the hot side surface may be open to atmosphere or thermally coupled to a passive cooling device, such as a heat sink, and/or to an active cooling device 114, such as a fan. Each TEC 112 or cooling element may be powered by any suitable power source, such as a battery 108 or fuel cell 108.

Figure 2:
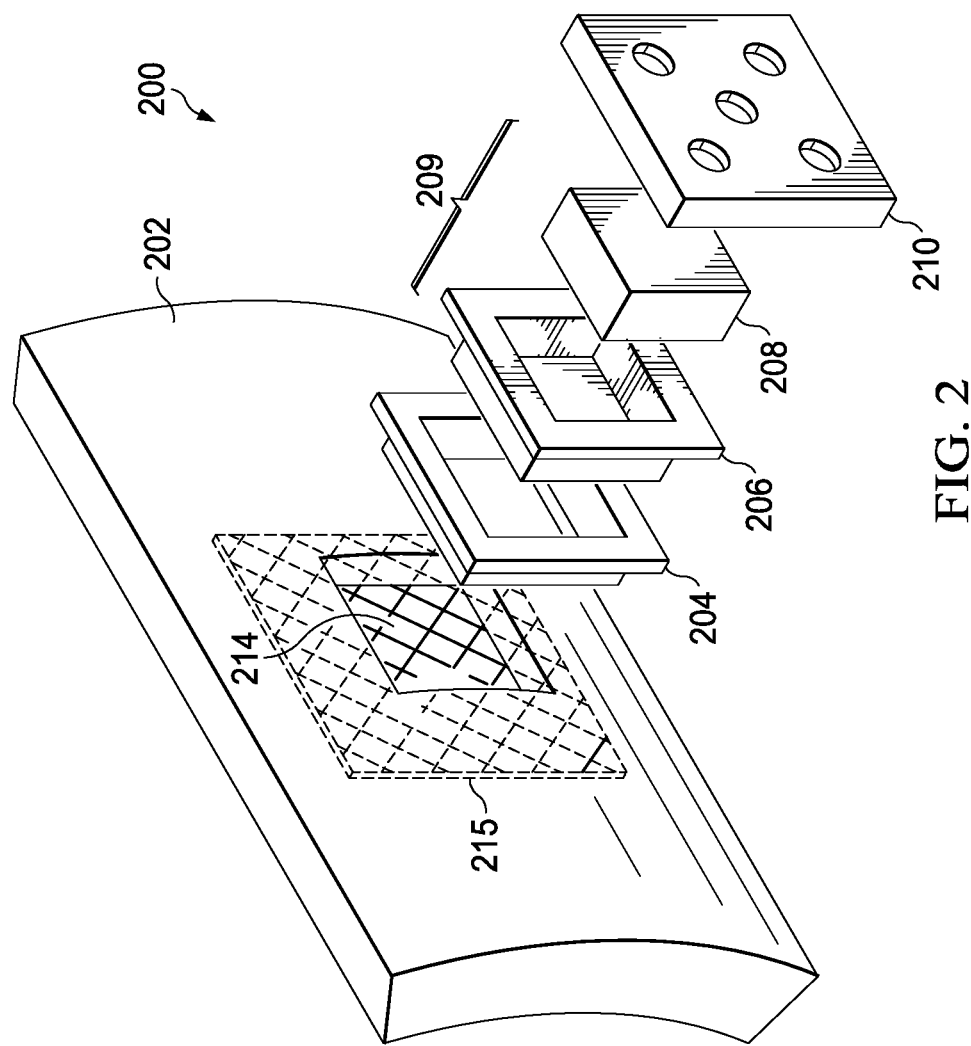
FIG. 2 illustrates an exploded view of an embodiment of a prosthesis cooling system module.

As may be seen in the embodiment of FIG. 2, a modular prosthesis cooling system 200 may comprise one or more housing components configured for permanent, semi-permanent or removable mounting to a prosthesis socket 202, and one or more cooling components configured for removable mounting to the prosthesis socket 202. Such a system may be retro-fitted to a fabricated prosthesis socket, or be installed during fabrication of a prosthesis socket. In the embodiment in FIG. 2, a port 204 may be permanently or semi-permanently embedded in a prosthesis socket 202. A socket aperture 214, or window, may be formed in the socket wall to receive the port 204. A plug 206 having a TEC 208 and/or other cooling components mounted thereto may form a plug module 209 configured for removable mounting to the port 204. A shroud 210 may be disposed to substantially cover the plug 206 and TEC 208.

Figure 3:
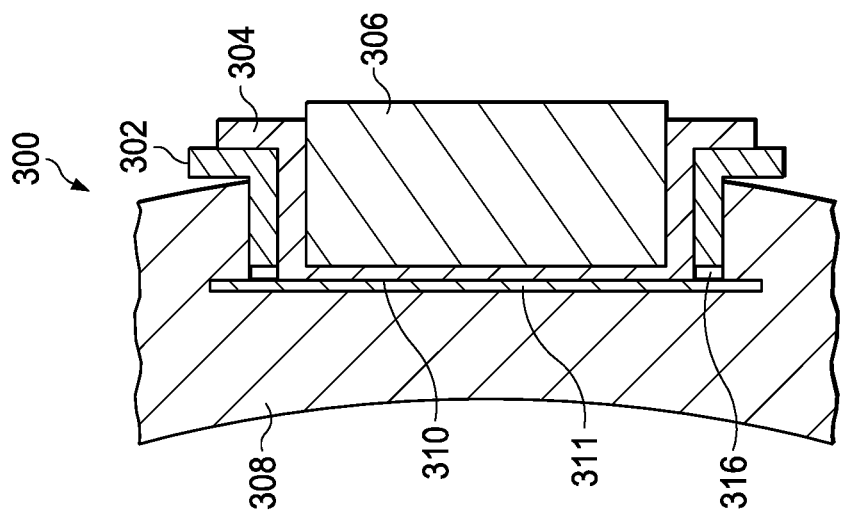
FIG. 3 illustrates a section view of an embodiment of a socket wall having mounted thereto a prosthesis cooling system module.

In some embodiments, a heat-conductive layer 215 may be provided in the socket aperture 214. In other embodiments, the prosthesis socket 202 may be provided with a heat-conductive layer 215 disposed between the liner and the cooling component. A heat-conductive layer 215 may be a full or substantially full layer of a prosthesis socket, such as shown in FIG. 2, or a partial layer of a prosthesis socket 202, such as shown in FIG. 3. A heat-conductive layer 215 may be added to or exposed by formation of a socket aperture 214, or may be included during fabrication the prosthesis socket. In other embodiments, a prosthesis socket may be fully or partially lined with a heat-conductive layer, which may be continuous or discontinuous, depending on the size, location and number of TECs used for cooling the prosthesis socket. The heat conductive layer may be a base layer of the socket, or an intermediate layer of the socket. In such embodiments, the socket aperture 214 may be formed so as to expose the heat conductive layer 215 such that a plug module 209 may be placed in a heat exchange relationship therewith.

The heat-conductive layer 215 may comprise a mesh, foil, thin plate, plastic, carbon fiber, fabric, foam or any other thermal conductive material capable of formation in a prosthesis socket. For example, a copper or aluminum mesh or foil may be used as a heat-conductive layer 215. A heat-conductive layer 215 may be provided to de-localize the cooling effect of the cooling components. A heat-conductive layer 215 may serve as a cold sink for heat built up in the prosthesis socket. A heat-conductive layer 215 may provide a larger cooling surface area, thus augmenting the cool surface area of a TEC 208. A heat-conductive layer 215 may also bridge or thermally connect more than one TEC 208, thus effectively providing a more thermally-uniform cooling surface on the interior of a prosthesis socket.

Similarly, a heat conductive layer (not shown) as described above may be provided on the outer surface of a prosthesis socket and configured for a heat-exchange relationship with the hot side of a TEC. A heat conductive layer so disposed may serve as a heat sink, or part of a heat sink, for a TEC plug mounted to a prosthesis socket. As may be apparent, more than one heat conductive layer may thus be used in connection with a TEC: one heat conductive layer in a heat-exchange relationship with the cold side of a TEC, and the other heat conductive layer in a heat-exchange relationship with the hot side of a TEC.

These system components may comprise any suitable material, such as thermoplastic walls and a thermally conductive base that touches part of the socket wall. The components may be constructed entirely of a thermally conductive material such as aluminum or copper. The components may be constructed of a composite where two or more constituent materials are combined to create an individual component such as carbon fiber. The port 204 may be designed to be coupled to the prosthetic socket 202. The plug 206 may be designed to hold a TEC 208 and/or other cooling components. The plug 206 may be designed to removably couple with the port 204, and may provide a secure and thermally-conductive interface for the TEC 208 and/or cooling components with the interior wall of the prosthesis socket 202.

FIG. 3 illustrates an embodiment of a port 302, plug 304, and TEC 306 assembled to form a cooling system 300. The port 302 may be installed in the prosthesis socket wall 308. The TEC 208 may comprise a TEC, and may in some embodiments, further comprise a passive and/or active heat dissipation unit (not shown separately), such as a heat sink and/or fan, each fitted to the plug 304. The plug 304 and TEC 306 may comprise a plug module. In this embodiment, the socket 308 may have formed therein an aperture 310 that allow for interface between the port 302, plug 304, and socket wall 308. The aperture 310 may allow extra space 316 for a thermal adhesive, thermal paste, or other thermal material that may be used to enhance heat transfer between the cooling system 300 and the socket wall 308, which may comprise a heat-conductive layer 311. The aperture 310 may be formed during fabrication of the prosthesis socket, or be formed in a completed prosthesis socket by removing socket wall 308 material using any suitable material removal method, such as cutting, filing or drilling.

Figure 4:
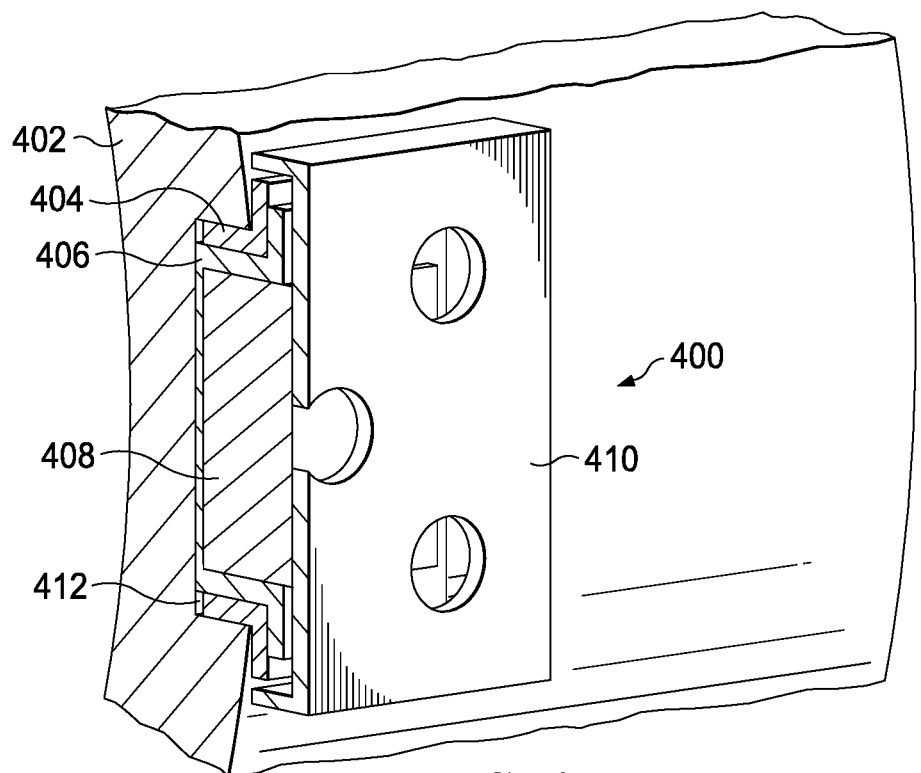
FIG. 4 illustrates a section view of an embodiment of a socket wall having mounted thereto a prosthesis cooling system module including a removable shroud.

FIG. 4 illustrates an embodiment of a modular prosthesis cooling system 400 that comprises a port 404, a plug 406, a cooling component 408, and a shroud 410. In this embodiment, the shroud 410 may be configured to allow air flow between the atmosphere and the cooling component 408. If a heat dissipation device is used, such as a heat sink and/or fan thereof, the shroud 410 may allow air to circulate to the heat dissipation device as well as protect those elements from damage by impact. The shroud 410 may have one or more vents formed therein that may be designed for maximizing airflow to and from of the cooling component 408. The location, shape and size of these vents may vary depending upon the airflow requirements to achieve desired heat transfer. As with the embodiment of FIG. 3, a space 412 may be left between parts of the cooling system 400 and socket 402. This space 412 may be filled in with a thermally conductive material such as thermal grease or other high heat transfer material.

Figure 5:
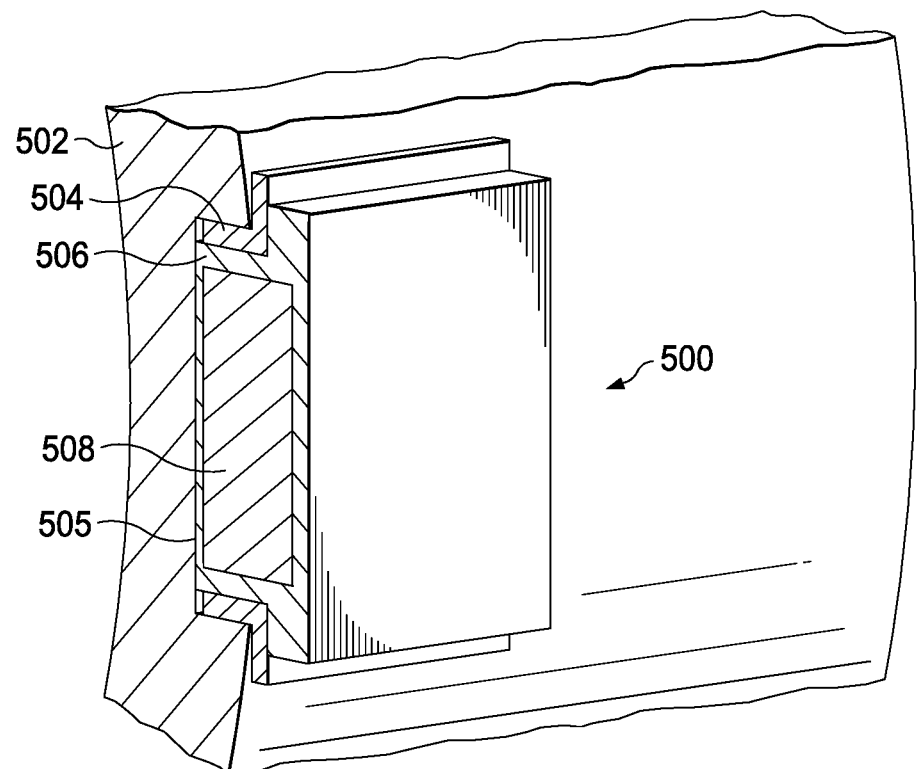
FIG. 5 illustrates a section view of an embodiment of a socket wall having mounted thereto a prosthesis cooling system module including an integral shroud.

FIG. 5 illustrates an embodiment of a cooling assembly 500 having a plug 506 configured to completely contain a cooling component 508 and interface with a port 504. The port 504 may be disposed in an aperture 505 in the socket wall 502 formed to receive the port 504. In this embodiment, the plug 506 may comprise a protective shroud integrated thereto. This embodiment may include similar shroud features as mentioned in connection with FIG. 4, such as vents designed for maximizing airflow in and out of the cooling elements and for providing protection to the cooling elements from impact.

A port as described herein may be disposed in an aperture formed in the socket. This aperture may be formed during prosthesis socket fabrication, or be formed after socket fabrication by removing socket material. The socket material may be removed by cutting, drilling, sanding, or other suitable method of material removal. The port may be coupled to the prosthetic socket through the use of any suitable fastener or method, such as threaded inserts in the socket wall and threaded fasteners such as screws to connect the housing and the socket, or adhesives, or magnets, or friction fit. The threaded inserts may rest inside an aperture created specifically for the threaded inserts, and the threaded inserts may be bonded to the socket. The threaded inserts may be bonded to the socket by use of an adhesive, epoxy, glue, or cement. The port or threaded inserts may also be held in place by compression from an outside restraint that wraps fully or partially around the socket. Straps, elastic bands, magnets, hook-and-loop fastener, or other restraints may be used to secure the port or threaded inserts inside the aperture formed in the socket wall. External restraints may wrap fully around the socket, or have part of the external restraint secured to the socket wall. External restraints may be secured to the socket wall via adhesive, friction fit, fasteners, or built into the socket wall during fabrication.

The interface between the port and plug module may be secured by the use of threaded fasteners such as screws or bolts. The interface may also be secured by use of other means such as clips, plugs, friction fit, pins, magnets, and adhesives. The interface may also use a threaded port and threaded plug, where the port and plug interface via cooperating threads. The port and plug module may also be sealed via insertion of an o-ring, face gasket, or other means of creating an air-tight or water-tight seal between components. The o-ring or gasket material may be a polymer or metal that compresses during the process of securing the port and plug together to create an air- or water-tight seal.

The plug module may include the TEC, heat sink, fan, or other components necessary to facilitate the transfer of heat from the hot side of the TEC to atmosphere or other heat sink. The TEC, heat sink and/or fan may be secured together using an adhesive, a compressive force applied by threaded fasteners, magnets, elastic, or hook-and-loop fasteners, or compressive forces created by coupling the port and plug together. A shroud housing component may be used to create a protective and aesthetically pleasing interface between the port, plug module and the user. A shroud may be attached to the port and plug module by means of adhesive, bolts or screws, magnets, hinges, slidable engagement, spring loaded clips, or a compressive force applied by straps, for example. The shroud may be composed of a variety of shapes, materials, and components. The shape of the shroud may vary, but the protective nature may remain the same across different embodiments. The shroud shape may also vary and be square or circular to mirror the shape of the port and plug module. The shroud may or may not completely hide the port and plug module from view. The shroud may or may not make contact with the prosthetic socket wall and only make contact with the port or plug. In another embodiment, the shroud may or may not make contact with the port or plug, and only make contact with the socket wall. The shroud may be designed to prevent objects from coming in contact with the plug module, and may allow for intake and exhaust air to flow through the heat sink and/or fan.

The port and plug module may be mounted to the socket in a variety of ways, depending on socket configuration and patient needs. Prosthesis sockets vary by layers, materials, voids, or structural elements incorporated into the socket design. In some embodiments, the port and plug may be directly mounted to the prosthesis socket so that the base of the port and plug interface directly with the socket liner or inner layer of the socket wall. In other embodiments, the port and plug may be separate from the residual limb and liner by several layers of socket wall.

During socket fabrication, a prosthetist may use a dummy spacer or plastic model to form an aperture in the socket wall to receive the cooling system. The port may be mounted in the aperture and bonded in place with a suitable bonding agent, such as thermal or structural epoxy. Small diameter tubing may be embedded or formed in the socket wall to provide channels for routing wire leads from a power supply to the cooling system.

Although the disclosed subject matter and its advantages have been described in detail, it should be understood that various changes, substitutions and alterations can be made herein without departing from the invention as defined by the appended claims. Moreover, the scope of the claimed subject matter is not intended to be limited to the particular embodiments of the process, machine, manufacture, composition, or matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods or steps.

What is claimed is:

1. A method of mounting a thermoelectric cooling component to the socket of a prosthesis, the method comprising:
   forming an aperture in a prosthesis socket, the aperture being configured to receive a port;
   mounting a port to the aperture; and
   mounting a plug module in the port so that the plug module is removable without compromising the structural integrity of the prosthesis socket, the plug module comprising a thermoelectric cooling component oriented to transfer heat away from a residual limb.

2. The method of claim 1, further comprising disposing a shroud over the plug module, the shroud being configured to allow heat to dissipate from the plug module.

3. The method of claim 1, further comprising:
   forming a channel in the prosthesis socket extending from the aperture to the exterior of the socket; and
   routing electrical leads of the thermoelectric cooling component through the channel.

4. The method of claim 1, further comprising providing a heat conductive layer for the prosthesis socket, the first heat conductive layer being in a heat-exchange relationship with the plug module.

5. The method of claim 1 wherein mounting the port to said aperture includes coupling the port to said prosthesis socket through use of one or more fasteners.

6. The method of claim 5 wherein the one or more fasteners are threaded inserts.

7. The method of claim 6 wherein said threaded inserts are bonded to said prosthesis socket by use of an adhesive, epoxy, glue or cement.

8. The method of claim 6 wherein said port is held in said aperture by compression from an outside restraint that wraps fully or partially around said prosthesis socket.

9. The method of claim 8 wherein said outside restraint is secured to a socket wall.

* * * * *